(12) United States Patent
Kimmel

(10) Patent No.: US 12,161,816 B2
(45) Date of Patent: Dec. 10, 2024

(54) STEERABLE SHEATH DEFLECTION MECHANISM

(71) Applicant: Imricor Medical Systems, Inc., Burnsville, MN (US)

(72) Inventor: Scott Kimmel, St. Paul, MN (US)

(73) Assignee: IMRICOR MEDICAL SYSTEMS, INC., Burnsville, ME (US)

( * ) Notice: Subject to any disclaimer, the term of this patent is extended or adjusted under 35 U.S.C. 154(b) by 806 days.

(21) Appl. No.: 17/312,825

(22) PCT Filed: Dec. 12, 2019

(86) PCT No.: PCT/US2019/065922
§ 371 (c)(1),
(2) Date: Jun. 10, 2021

(87) PCT Pub. No.: WO2020/123774
PCT Pub. Date: Jun. 18, 2020

(65) Prior Publication Data
US 2022/0054800 A1   Feb. 24, 2022

Related U.S. Application Data

(60) Provisional application No. 62/869,132, filed on Jul. 1, 2019, provisional application No. 62/779,130, filed on Dec. 13, 2018.

(51) Int. Cl.
*A61M 25/01* (2006.01)

(52) U.S. Cl.
CPC .... *A61M 25/0147* (2013.01); *A61M 25/0136* (2013.01); *A61M 2025/015* (2013.01); *A61M 2025/0161* (2013.01)

(58) Field of Classification Search
CPC .......... A61M 25/0147; A61M 25/0136; A61M 2025/015; A61M 2025/0161
See application file for complete search history.

(56) References Cited

U.S. PATENT DOCUMENTS 4,203,430 A     5/1980  Takahashi
4,711,030 A  *  12/1987 Ruston, Sr. ............. B26B 7/005
                                              30/DIG. 1

(Continued)

FOREIGN PATENT DOCUMENTS

| DE | 2752325 A1 | 7/1978 |
| WO | 2014093457 A1 | 6/2014 |
| WO | 2016118426 A1 | 7/2016 |

OTHER PUBLICATIONS

International Search Report issued in PCT/US2019/065922 dated Mar. 18, 2020.

*Primary Examiner* — Nathan R Price
*Assistant Examiner* — John A Doubrava
(74) *Attorney, Agent, or Firm* — Fox Rothschild LLP; Carol Thorsyad-Forsyth

(57) ABSTRACT

A steerable sheath with a deflection mechanism assembly is provided. The assembly includes a tubular shaft that receives first and second longitudinal movement wires at a distal end. A control handle includes a main body configured to receive first and second bevel gears. The first longitudinal movement wire is coupled to the first bevel gear and the second longitudinal movement wire is coupled to the second bevel gear. A rotatable adjustment knob is engageable with the control handle and has an external geared portion matingly engageable with the first and second bevel gears and the rotatable adjustment knob is moveable between a first and second position.

19 Claims, 19 Drawing Sheets

(56) References Cited

U.S. PATENT DOCUMENTS

| | | | | |
|---|---|---|---|---|
| 5,987,344 | A | * | 11/1999 | West .................. A61M 25/0144 606/41 |
| 6,228,032 | B1 | | 5/2001 | Eaton et al. |
| 6,485,455 | B1 | * | 11/2002 | Thompson ............... A61N 1/06 604/95.04 |
| 9,095,682 | B2 | | 8/2015 | Romoscanu |
| 9,737,688 | B2 | | 8/2017 | Furnish |
| 2004/0222314 | A1 | * | 11/2004 | Chappell ................ A01G 25/00 239/542 |
| 2008/0287741 | A1 | * | 11/2008 | Ostrovsky ......... A61M 25/0141 600/141 |
| 2016/0193449 | A1 | | 7/2016 | Sarabia et al. |
| 2016/0206853 | A1 | * | 7/2016 | Bolduc ............. A61M 25/0136 |
| 2017/0189664 | A1 | * | 7/2017 | Oliverius .............. A61M 39/10 |
| 2017/0291008 | A1 | * | 10/2017 | Hillukka ........... A61M 25/0074 |
| 2019/0117937 | A1 | * | 4/2019 | Humphrey ........ A61M 25/0147 |

\* cited by examiner

STEERABLE SHEATH DEFLECTION MECHANISM

CROSS-REFERENCE TO RELATED APPLICATIONS

The present application is a U.S. National Phase of International Patent Application No. PCT/US2019/065922 filed on Dec. 12, 2019, which claims priority to U.S. Provisional Patent Application No. 62/869,132 filed on Jul. 1, 2019 and U.S. Provisional Patent Application No. 62/779,130 filed on Dec. 13, 2018. The contents of the listed patent documents are incorporated herein by reference in their entireties.

FIELD OF THE INVENTION

This invention is directed to steerable sheaths. In particular this is directed to a steerable sheath deflection mechanism and its method of use.

BACKGROUND OF THE INVENTION

Steerable sheaths are known. A conventional steerable sheath as a distal section that bends when the user actuates a mechanism in the control handle. The mechanism in the handle along with the means of transferring a force to the distal section of the sheath can be referred to as a deflection mechanism. The deflection mechanisms consists of two parts: the control handle assembly and the transfer assembly, located in the sheath shaft.

Typical steerable sheath control handle assemblies involve a knob component that when rotated, transfers rotational movement to a component that translate in a linear fashion along the long axis of the steerable handle. These are rotation to linear translation mechanisms. The function of the liner component is to apply a tensioning force on a pull wire, which causes the pull wire translate in the proximal linear direction. At the distal end, the pull wire is connected to the tip of the sheath, usually via a pull ring. When the pull wire translates linear proximal direction, the tensioning force is transferred to the pull ring and this in turn causes the tip of the sheath to deflect. Usually, the linear translating component is a lead screw or rack that has some variation of external threads that interface with internal threads on the rotation knob. The drawback of such rotation to linear mechanisms is that if the pull wire must be translated to a large degree (high degree of tip deflection), the control handle geometry must accommodate the corresponding large degree of linear translation required of the linear component. This requires the sheath handle to have a very long length and sometimes a larger outer diameter. Adding length to the sheath handle requires adding length to the shaft of the corresponding therapy device that will be inserted into the sheath. This is not a critical problem company that produces the sheath also produces the therapy catheter. But in situations where the intent is that the sheath be used with therapy catheters from other companies, a sheath handle that is too long may inhibit sheath compatibility and utility. Also, the therapy device usually has a longer handle, so adding a long sheath handle to the procedure can make the situation unwieldy for the clinician. Finally, the larger OD of the sheath handle is not ideal from an ergonomics perspective.

Another disadvantage of the traditional rotation knob to liner mechanism is that the ideal pitch for the thread on the knob and the linear mechanism seems to be about 0.4 or 0.5 inches. If the pitch is greater than this, the amount of friction force required to hold the knob in place during large shaft deflections becomes so high that it becomes difficult to turn the knob. The problem with this pitch value, though, is that if more than 0.4 or 0.5 inches of translation of the pull wire is required to fully deflect the sheath, more than one knob rotation is required. This is less than ideal to the user because he/she may have to deflect the knob many times during a long procedure and his/her hand can suffer fatigue or in extreme situations, repetitive stress injuries.

In addition size and length issues posed by the rotation to linear translating mechanism, very complex mechanisms have been developed to achieve linear translation and overcome a crowded IP landscape. But complex mechanisms equate to multiple components that increase device assembly time and ultimately leads to increased device cost.

Typically, steerable sheath transfer assemblies involve one or more pull wires that are attached to the handle assembly proximally and attached to a pull ring distally. Most often, the pull wires and pull ring are composed of metallic materials, such as stainless steel, Pt-IR, and like materials, and the pull wires are welded to the pull ring.

One drawback of the standard transfer assembly design is that it is not MR compatible due to the long metallic pull wire. To make the transfer assembly MR compatible, the metallic pull wire must be replaced with a polymeric pull wire. As a result, it is extremely difficult to bond this polymeric pull wire to a metallic pull ring. One potential method is to loop the pull wire around the pull ring, but this creates locations where the pull wire undergoes abrasion during repeat sheath deflections. This abrasion will eventually lead to pull wire failure and the loss of the user's ability to deflect the distal section of the sheath. Another method is to use an adhesive to bond the pull wire to the pull ring. It is challenging, however, to discover an adhesive that can adequately and reliably bond a polymer to metal. One solution to the adhesive challenge is to also replace the metallic pull ring with a polymeric pull ring. It is then easier to find an adhesive that will bond the polymeric pull wire to a polymeric pull ring, but the polymeric pull ring requires a thicker wall to achieve the strengths achieved by a metallic pull ring. The thicker walled polymeric pull ring causes the outer diameter of the sheath to increase which is not ideal as clinicians prefer to use steerable sheaths with the smallest possible outer diameter. Additionally, it is extremely difficult to get the adhesive bond between the polymeric pull ring and pull wire to have the same tensile strength as the weld bond between the metallic pull ring and pull wire.

Thus, what is needed is a steerable sheath deflection mechanism that overcomes the limitations associated with the standard handle assembly outlined above. Further, there is also a need for a deflection mechanism with a transfer assembly that will allow a steerable sheath to be MR compatible but will have equivalent mechanical characteristics to the metallic transfer assembly.

BRIEF SUMMARY OF THE INVENTION

The foregoing needs are addressed by the device and method in accordance with the invention.

In one aspect of the invention, a deflectable sheath assembly is provided that includes a tubular shaft that receives first and second longitudinal movement wires at a distal end. A control handle includes a main body configured to receive first and second bevel gears. The first longitudinal movement wire is coupled to the first bevel gear and the second longitudinal movement wire is coupled to the second bevel gear.

In another aspect of the invention, a rotatable adjustment knob is engageable with the control handle, the rotatable adjustment knob having an external geared portion matingly engageable with the first and second bevel gears and the rotatable adjustment knob is moveable between a first and second position.

In another aspect of the invention, the adjustment knob is rotatable to the first position which causes engagement of the gear on the outer surface of the first bevel gear and causes the first bevel gear to rotate in a direction that causes the first longitudinal pull wire to wrap around a circumferential surface of the first bevel gear and cause proximal longitudinal movement of the first longitudinal movement wire.

In another aspect of the invention, when the adjustment knob is rotated to the first position it also causes engagement of the gear on the outer surface of the second bevel gear and causes the second bevel gear to rotate in a direction that causes the second longitudinal pull wire to unwrap around a circumferential surface of the second bevel gear, whereby tension is released on the second longitudinal movement wire.

In another aspect of the invention, when the adjustment knob is rotated to the second position it causes engagement of the gear on the outer surface of the second bevel gear and causes the second bevel gear to rotate in a direction that causes the second longitudinal pull wire to wrap around a circumferential surface of the second bevel gear and causes proximal longitudinal movement of the second longitudinal movement wire.

When the adjustment knob is rotated to the second position it also causes engagement of the gear on the outer surface of the first bevel gear and causes the first bevel gear to rotate in a direction that causes the first longitudinal pull wire to unwrap around a circumferential surface of the first bevel gear, whereby tension is released on the first longitudinal movement wire.

In another aspect of the invention, the proximal longitudinal movement of the first longitudinal movement wire causes the distal end of the steerable sheath to deflect from a longitudinal axis of the tubular shaft in a first direction.

In another aspect of the invention, the proximal longitudinal movement of the second longitudinal movement wires causes the distal end of the steerable sheath to deflect from a longitudinal axis of the tubular shaft in a second direction.

In another aspect of the invention, the first proximal longitudinal movement wire is looped around and encased within the wall of the distal section of the tubular shaft.

In another aspect of the invention, the second proximal longitudinal movement wire is looped around the encased within the wall of the distal section of the tubular shaft.

In another aspect of the invention, the control handle includes two handle halves that are held together by a keystone component.

In another aspect of the invention, a wire housing component prevents the slack in the first and second tension wires from getting tangled in other handle components.

In another aspect of the invention, the tension wires are constructed of a flexible polymer such as Kevlar, Vectran, and similar materials. In other aspects, the tension wires are stainless steel or other metallic materials.

In other aspects of the invention, a wire-bridge component connects each metallic tension wire proximally to a flexible polymer tension wire and each flexible polymer tension wire wraps around the circumferential surface of each bevel gear.

In other aspects of the invention, the knob has an interference tab on its outer surface that contacts an interference tab on the handle stop to limit rotational travel of the knob. In other aspects of the invention, the interference tab on the knob does not contact the interference tab on the handle stop.

In other aspects of the invention, a floating stop component is disposed between the knob and the handle stop. In other aspects of the invention and interference tab is provided on the floating stop that contacts the interference tab on the knob and the interference tab on the handle stop and allows for the knob to rotate one or more revolutions before being stopped.

In other aspects of the invention, two or more floating stop components are disposed between the knob and the handle stop and thereby allow the knob to rotate two or more revolutions before being stopped.

In other aspects of the invention only one bevel gear is utilized to create a uni-directional sheath.

In other aspects of the invention, a second set of a knob, bevel gears, and tension wires creates a sheath that has quad-directional deflection.

In other aspect of the invention the rotation knob and each of the bevel gears has a gear ration that is not 1:1.

In other aspects of the invention, the gear ration between the rotation knob and the first bevel gear is different than the gear ration between the rotation knob and the second bevel gear.

In other aspects of the invention, the wrapping surface of the bevel gear has a non-circular shape such as a tear-drop, cam, and the like.

These and other aspects of the invention will now be described in detail.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
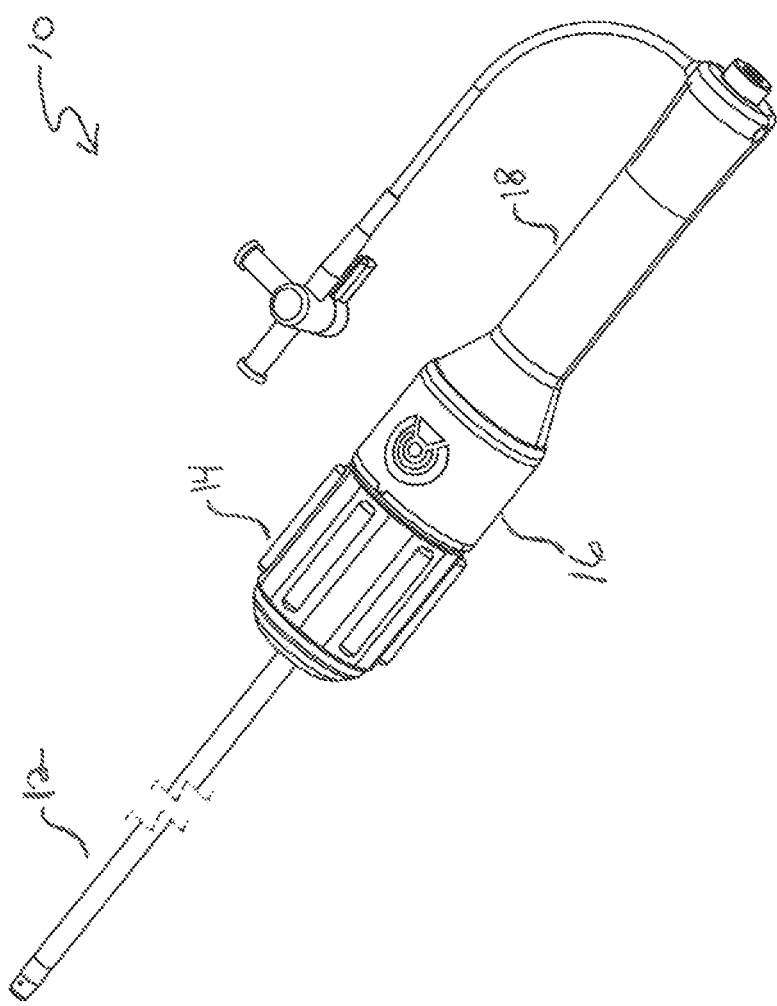
FIG. 1 is a perspective view of the steerable sheath in accordance with the invention showing the shaft, the knob, keystone and handle.
Figure 2:
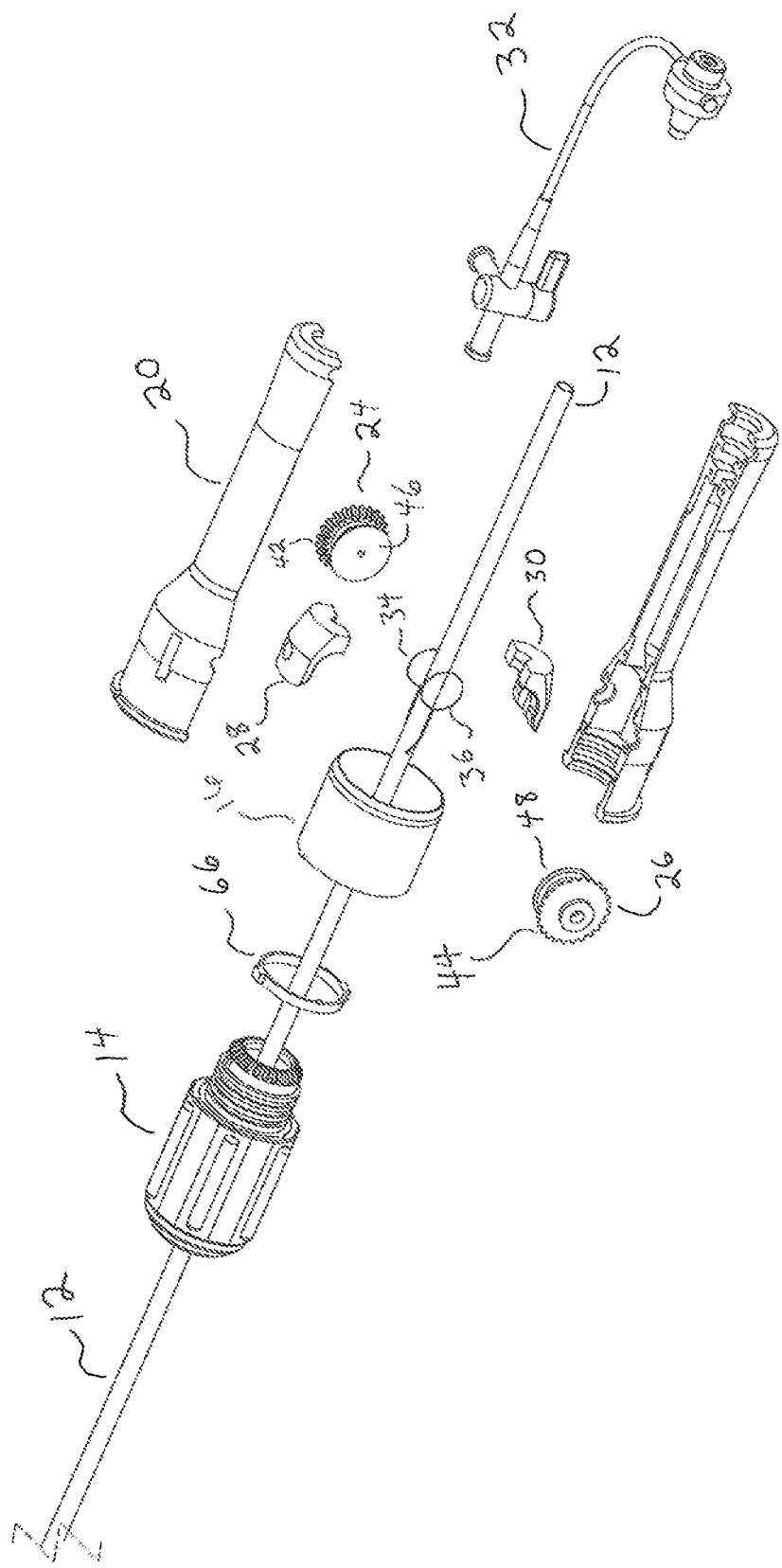
FIG. 2 is an exploded view of the steerable sheath in accordance with the invention.

Referring to FIG. 1, the device 10 is accordance with the invention broadly includes shaft 12, rotation knob 14, keystone 16 and handle 18. Handle 18 is constructed from first and second handle halves 20, 22 as best seen in FIG. 2. Keystone 16 is positioned over first and second bevel gears 24, 26, and first and second halves of pull wire housing 28, 30. Hemostasis valve assembly operable couples to shaft 12. Pull wire housing 28, 30 houses first and second pull wires 34, 36.

Figure 3:
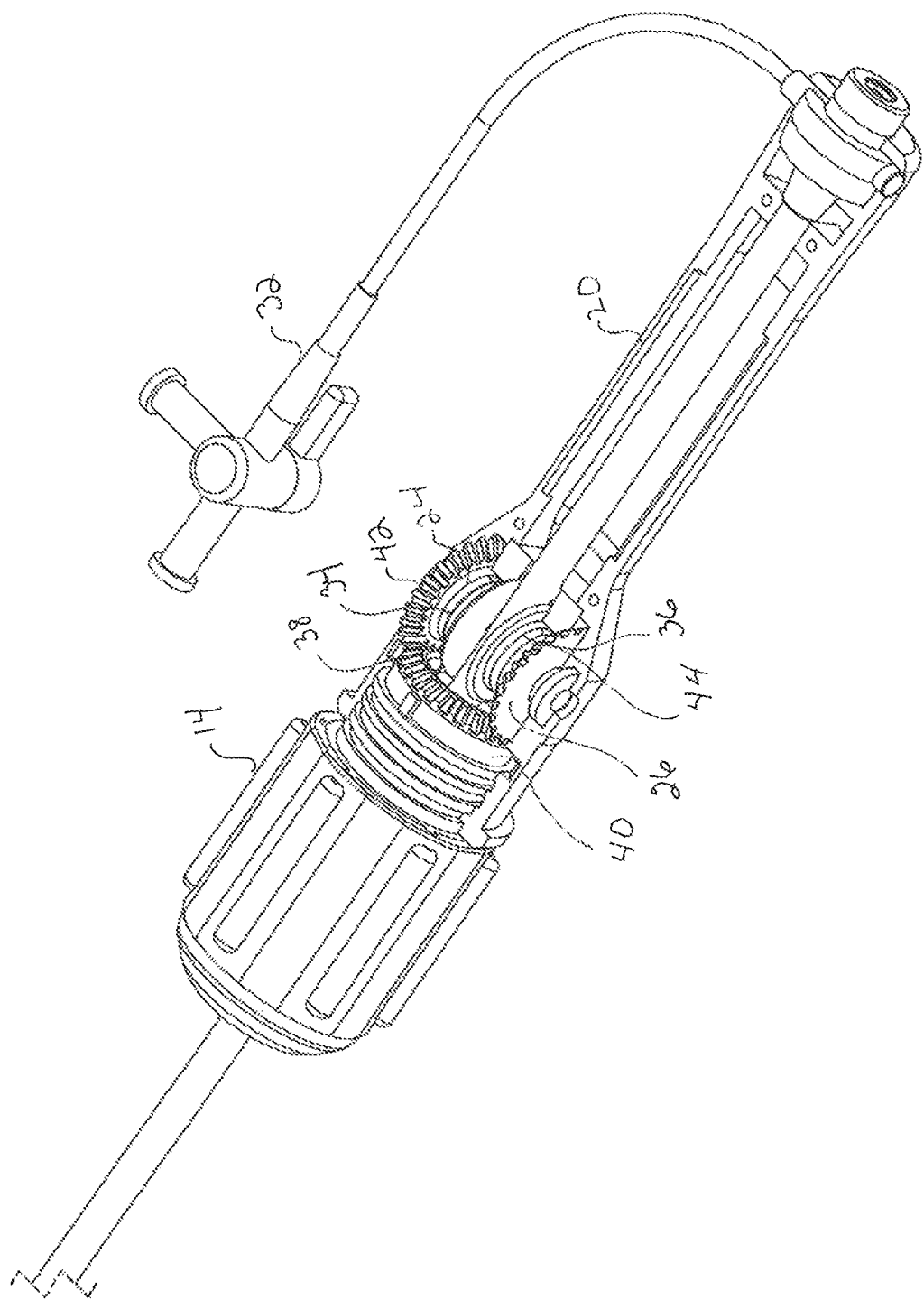
FIG. 3 is a view of the steerable sheath in accordance with the invention with one of the handle halves, pull wire housing, and the handle stop removed to show detail of the bevel gears and knob teeth.

Rotation knob 14 includes teeth 38 on the circumference of a proximal outer surface 40. The knob teeth 38 intermeshed with teeth on the bevel gears 24, 26 as best seen in FIG. 3. The knob 14 and bevel gears 24, 26 may have the same pitch diameter, meaning that there is a one-to-one rotation of the knob 14 and bevel gears 25, 26. In one aspect of the invention, the axis of rotation of the bevel gears 24, 26 is orthogonal to the axis of rotation of the rotation knob 14. Additionally, the axis of rotation of the bevel gears 24, 26 is co-linear, but the bevel gears 24, 26 are disposed in an opposite or mirror image position creating a right and left bevel gear 24, 26 respectfully. In this orientation, the respective inner faces 46, 48 of the bevel gears oppose each other and they are in a concentric position. When knob 14 is rotated, bevel gears 24, 26 rotate, but in opposite directions, because of the mirror image relationship.

Shaft 12 includes first and second (right and left) pull wires 34, 36 positioned thereon. Each pull wire 34, 36 is attached to one of the bevel gears 24, 26 respectively. The pull wire to bevel gear attachment is such that when the bevel gears rotate, the pull wires wrap around a designated circumferential surface of its respective bevel gear. This wrapping causes a tensioning force in the pull wire, which in turn causes the tip of the sheath to deflect to the right and the left as the case may be.

Those of skill in the art will appreciate that with conventional systems whichever direction and bevel gear may rotate, the wrapping action of the pull wires will occur, and the pull wires will be tensioned. This may create issues when trying to simultaneously apply tension to one pull wire and release tension on the other pull wire. The device 10 in accordance with the invention addresses this issue by pre-wrapping the pull wires 34, 36 around the respective bevel gears 24, 26 so that when the gear rotates in one direction, slack is created in the other pull wire so that no tensioning occurs. Pull wire housing 28, 30 insures that the slack of a particular pull wire does not become entangled in other components.

Those of skill in the art will appreciate that the two bevel gear 24, 26 rotation axes are perpendicular to the knob 14, so when the knob 14 rotates to the right or left, the bevel gears 24, 26 rotate up or down.

Thus in operation, when the knob 14 is in the neutral position, the right pull wire 34 is wrapped completely around the right bevel gear 24, and the left pull wire 26 is wrapped completely around the left bevel gear 36. When the knob 14 rotates to the right, the right bevel gear 24 rotates down. Correspondingly when the right bevel gear 24 rotates down, the right pull wire 34, which has already been wrapped around the right bevel gear 24 at least once, is further wrapped around the right bevel gear 24. A small rotation of the knob 14 would increase the amount of wire wrapped around the bevel gear from, for example, 1 complete wrap to 1.25 complete wraps and so forth. The pull wires 34, 36 do not necessarily get wound tighter, but rather more of each pull wire is being added to the circumference of the respective bevel gear 24, 26. When the knob 14 is rotated to the right of the tip of the sheath 12 moves to the right.

When the knob 14 is rotated to the left, the opposite happens (the left bevel gear 26 rotates down, and the right bevel gear 24 rotates up). The pre-wrap of the right pull wire 34 prevents it from tensioning when the right bevel gear 24 rotates up. If there were no pre-wrap, when the right bevel gear rotated up, it would cause pull or tension on the right pull wires would be pulled on at the same time.

As noted when the knob 14 is rotated to the right, the right bevel gear 24 rotates down and the right pull wire 34 is further wrapped around the bevel gear 24 creating tension on the right pull wire 24. In addition, when the knob 14 is rotated to the right, the left bevel gear 26 rotates up causing pre-wrapped left pull wire 36 to unwrap from the bevel gear 26, creating slack in the left pull wire 36. All of the foregoing allowing the tip of sheath 12 to move to the right.

When the knob 14 is rotated in the opposite direction, i.e. to the left, after being rotated to the right, the right bevel gear 24 rotates up so that its pull wire 34 is unwrapped creating slack in the right pull wire 34. The left bevel gear 26 rotates down, which causes the left pull wire 36 to further wrap around the left bevel gear 26, causing tension to be applied to the left pull wire 36 allowing the top of sheath 12 to move toward the left.

When the pull wire is under a large amount of tension, such as when the sheath tip is approximately more than 90 degrees deflected in the right or left direction, the respective pull wire imparts a torque force on the bevel gear which cause the bevel gear to impart a separation force on the two handle halves 20, 22 making it difficult for the handle halves to remain together if bonded only with adhesive or press fit together with mattel pins. This is overcome with the keystone component 16 in accordance with the invention, which is a hollow tube that is positioned over the two handle halves in the location of the two bevel gears. Those of skill in the art will appreciate that keystone component 16 is constructed of a rigid or semi-rigid material that is stronger than the separation force of the bevel gears 24, 26. The keystone component 16 mechanically holds the two handle halves 20, 24 together and overcomes the separation force so that the handle halves 20, 24 remain together.

Referring again to the FIGS. further details of the components of the knob to bevel gear sheath deflection mechanism will now be described. Referring to FIG. 3 a view of the knob to bevel gear sheath handle mechanism is shown. In this view, one of the handle halve, the handle s stop, and the pull wire housing has been removed and the intermeshing of the teeth 38 on the knob 14 with the teeth 42, 44 of the bevel gears 24, 26 is illustrated.

Figure 4:
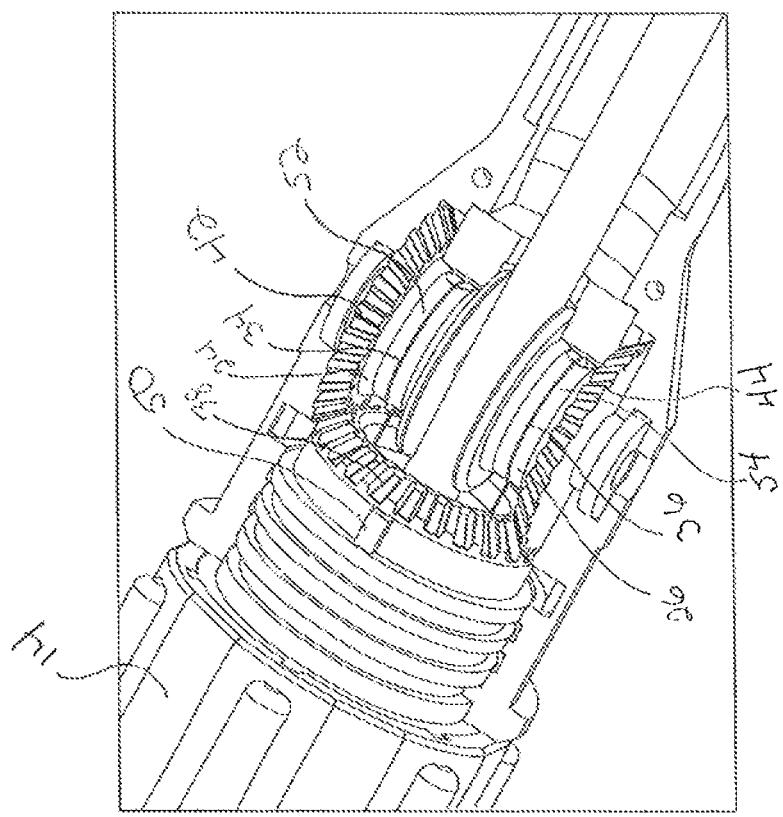
FIG. 4 is a view of the steerable sheath in accordance with the invention with one of the handle halves, pull wire housing, and the handle stop removed showing the pull wires when the knob is in the neutral position.

Referring now to FIG. 4, a close-up view of the knob to bevel gear sheath handle mechanism is depicted. This view demonstrates the configuration of the pull wires 34, 36 wrapped around the bevel gears 24, 26 when the knob 14 is in the neutral position as indicated by knob interference tab 50. Knob interference tab 50 engages with the handle stop (not shown in this view) interference tab 56, that prevents knob 14 from further rotation.

Figure 5:
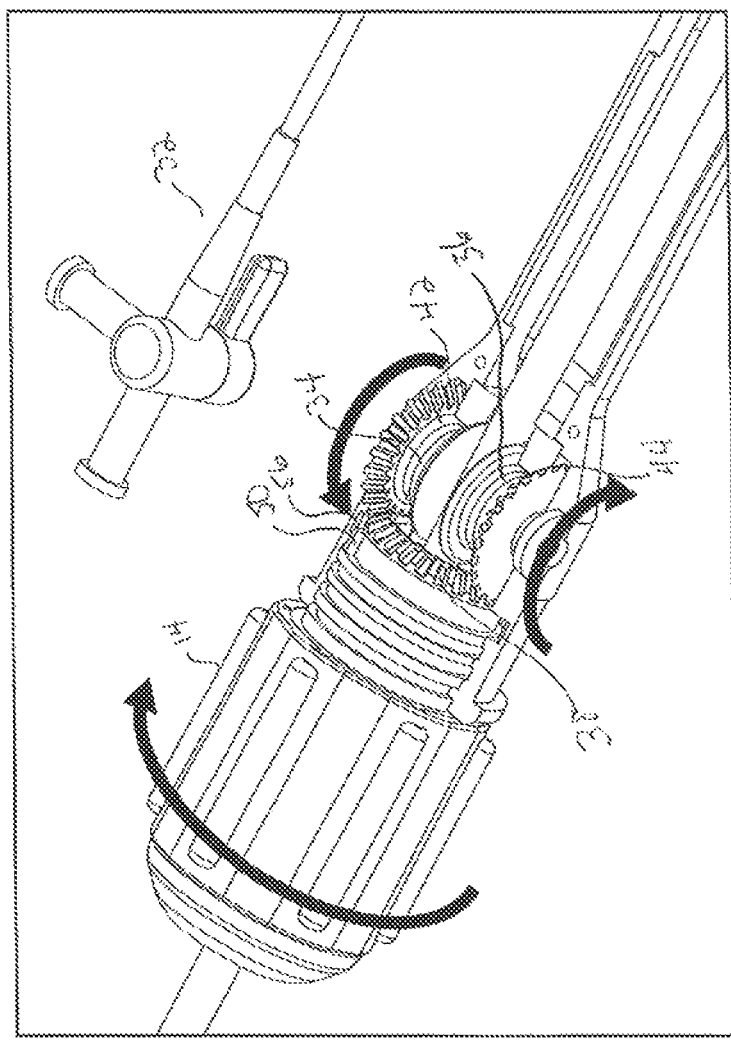
FIG. 5 is a view of the steerable sheath in accordance with the invention with one of the handle halves, pull wire housing, and the handle stop removed showing the rotation of knob to the right.

Referring now to FIG. 5 a view of rotation of the knob 14 to the right is illustrated. As previously disclosed, when the know 14 is rotated to the right, the right bevel gear 24 rotates down and creates tension on the right pull wire 34 as the right pull wire 34 wraps further around the right bevel gear surface 52. The left bevel gear 26 rotates up and because the left pull wire 36 has been pre-wrapped around the left bevel gear 26, slack is created in the left pull wire 36. When the knob 14 is rotated toward the left, the opposite occurs: slack is created in the right pull wire 34 and tension is created in the left pull wire 36.

Figure 6:
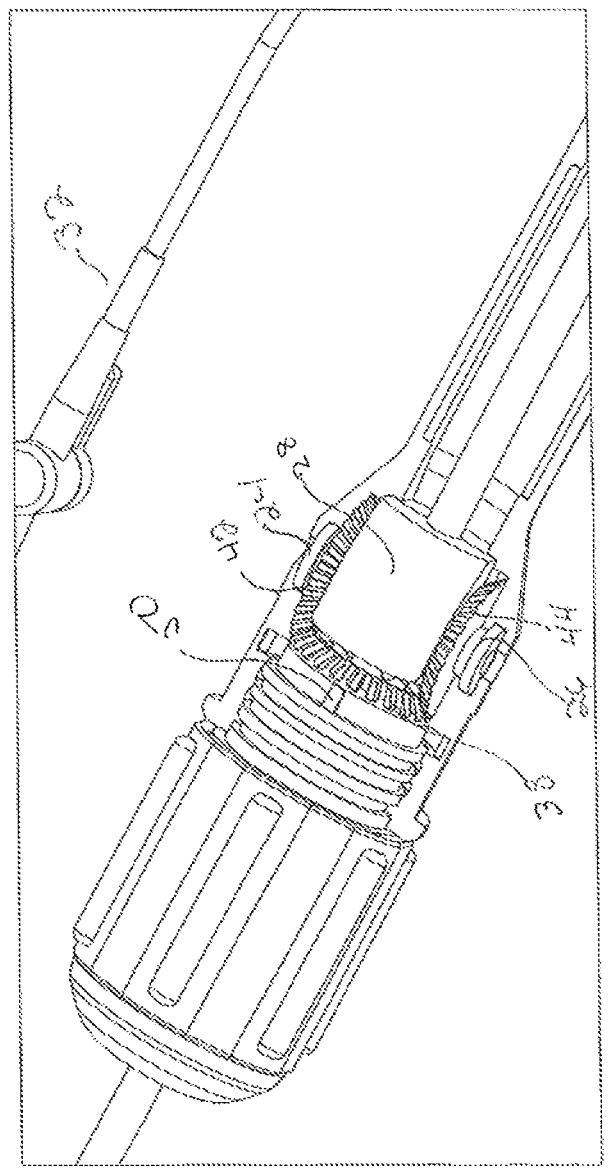
FIG. 6 is a view of the steerable sheath in accordance with the invention with one of the handle halves and the handle stop removed showing the pull wire housing for housing the first and second pull wires.

Referring now to FIG. 6 is a view of the steerable sheath in accordance with the invention showing the pull wire housing 28, 30 for housing the right and left pull wires 34, 36.

Figure 7:
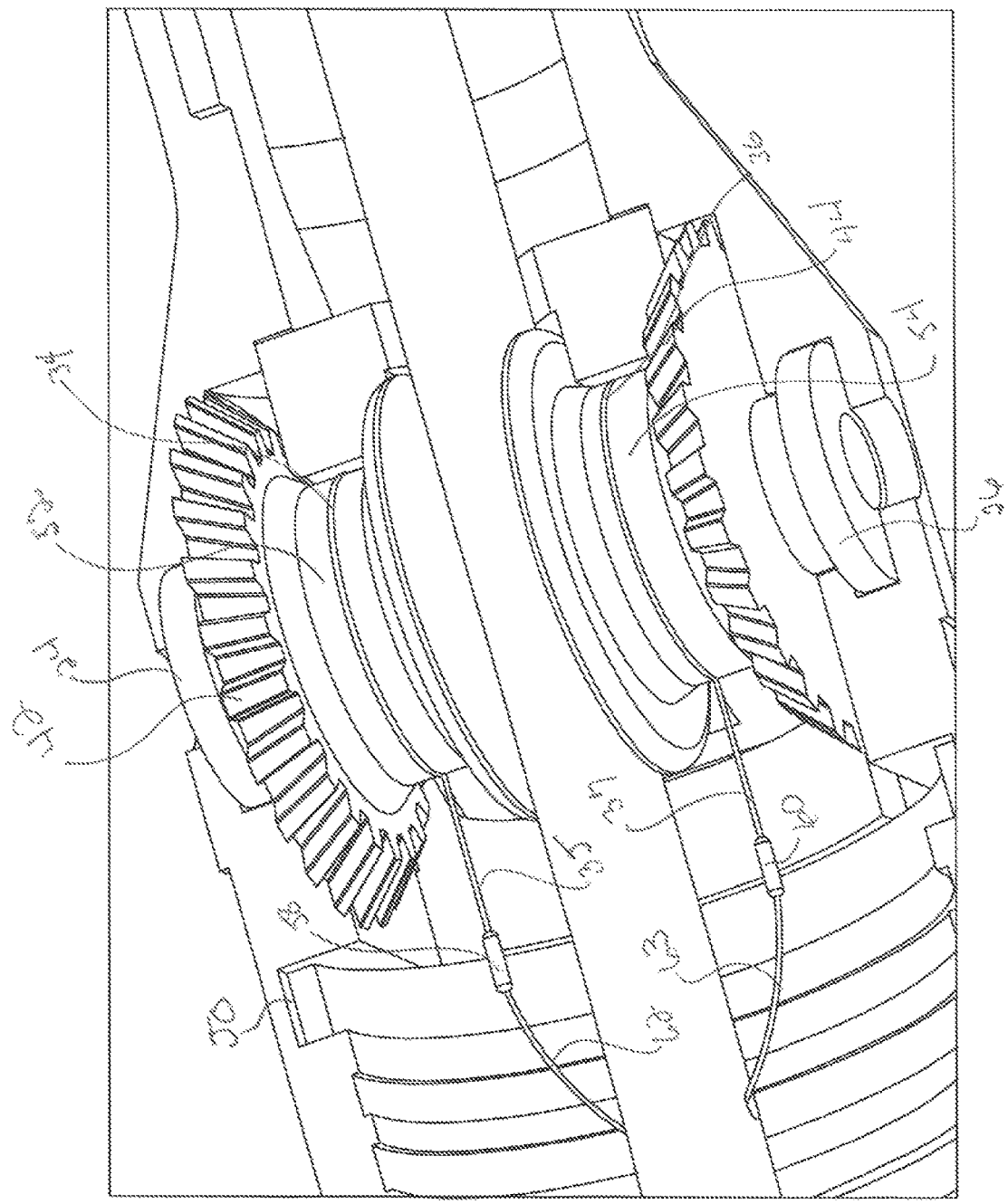
FIG. 7 is a view with one of the handle halves, pull wire housing, rotation knob, and the handle stop removed showing the wire-bridge component that connects each metallic tension wire to a flexible polymer tension wire with each flexible polymer tension wire wrapped around the circumferential surface of each bevel gear.

In one aspect of the invention, the right and left pull wires 34, 36 are composed of a flexible polymer, such as Kevlar or the like, which easily wraps around a surface 52, 54 of the right and left bevel gears, respectfully, as best seen in FIG. 7. Those of skill in the art will appreciate that this mechanism is difficult to implement in the traditional steerable sheath design which utilizes a stainless-steel pull wire. This difficulty arises from the fact that the stainless-steel wire is relatively stiff, and it would be difficult to wrap around a bevel gear of the smaller diameter that would be required in a sheath control handle. In another aspect, this limitation is overcome by the utilization of wire-bridge component 58, 60 that connects a stainless-steel pull wire 62, 63 to a short section of the more flexible polymer-based wires 34, 36. In this way, the pull wire any be constructed of stainless steel for most of the shaft, but at a point after it enters the control handle, the wire-bridge component 58, 60 would connect it to the polymer-based wires 34, 36, which would then be connected to the respective bevel gear 24, 26 is rotated, tension is applied to the polymer-based wires 34, 36, and this tension is then translated to the stainless-steel pull-wires 62, 63 through the wire bridge components 58, 60.

Figure 8:
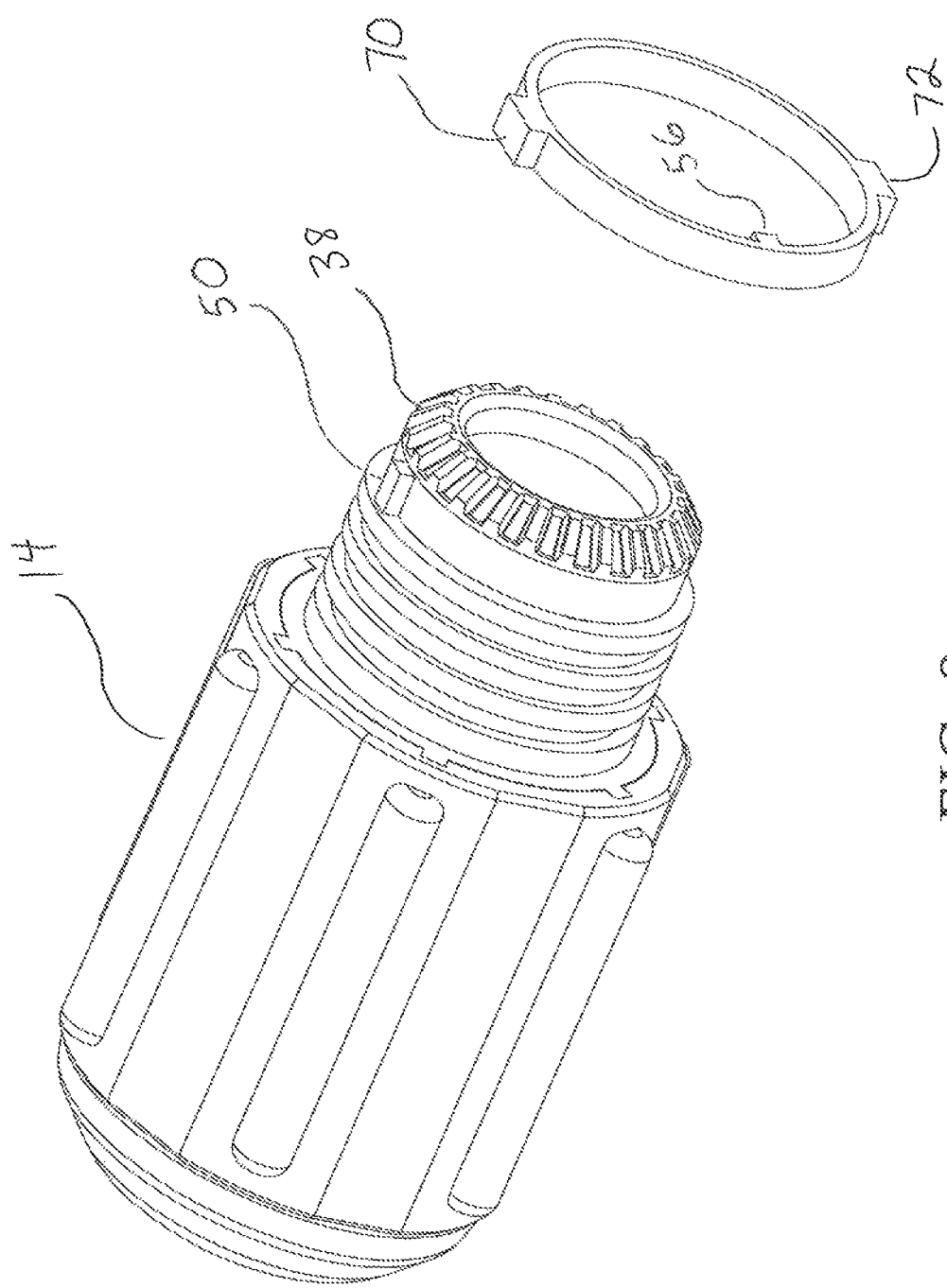
FIG. 8 is a partially exploded view of the knob showing the knob interference tab, and handle stop.

Another aspect of the design in accordance with the invention is limiting the amount of pull wire travel or the amount of sheath deflection. Clinicians are accustomed to a physical stop that limited the amount that the pull wire can travel and thereby limits the amount of distal sheath deflection. This keeps the clinician from 'over' deflecting the sheath and potentially damaging the sheath (pull wire snap) or damaging the indwelling device, such as the therapy catheter. With the standard rotation to the linear translating mechanism, the travel of the linear translating mechanism is contained in both directions. With the present knob to bevel gear design, the rotating movement of the either the knob 14 or the bevel gears 24, 26 must be constrained. Once method for achieving this is to place knob interference tab 50 on the outer surface of the knob 14 and place handle stop interference tab 56 on the inner surface of the handle stop 66 (as best seen in FIG. 8). Handle stop 66 engages handle 14 via outwardly extending mating features 70, 72.

As can be seen in FIG. 8, the handle stop interference tab 56 is keyed or notched so that when the knob interference tab 50 moves in either the right or left (clockwise or counterclockwide) direction, it engages the handle stop interference tab 56, which constrains the rotation movement of the knob 14. The knob interference tab 50 and the handle stop interference tab 56, together act as stops when they interfere with each other and in this manner, the rotation of the knob is constrained or limited.

Figure 9:
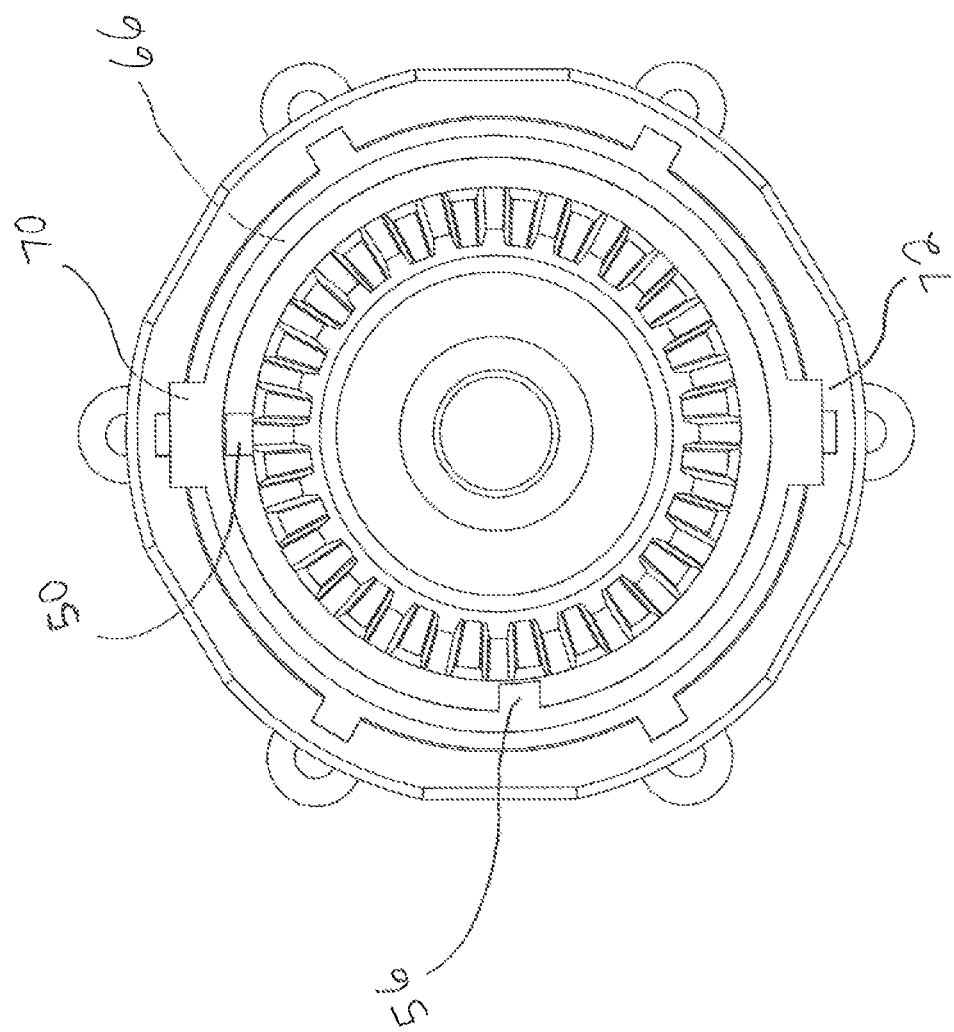
FIGS. 9-11 are front views of the knob showing the knob interference tab and handle stop in the starting position, rotated fully in the counterclockwise direction, and rotated fully in the clockwise position.
Figure 10:
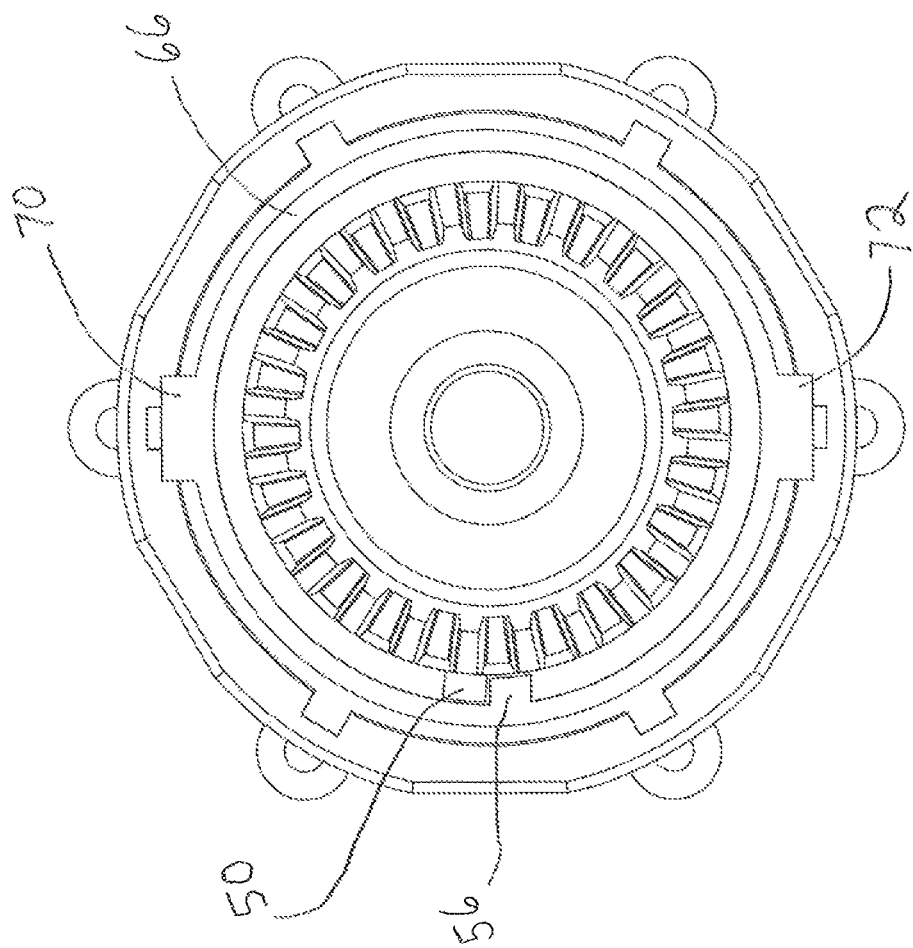
Figure 11:
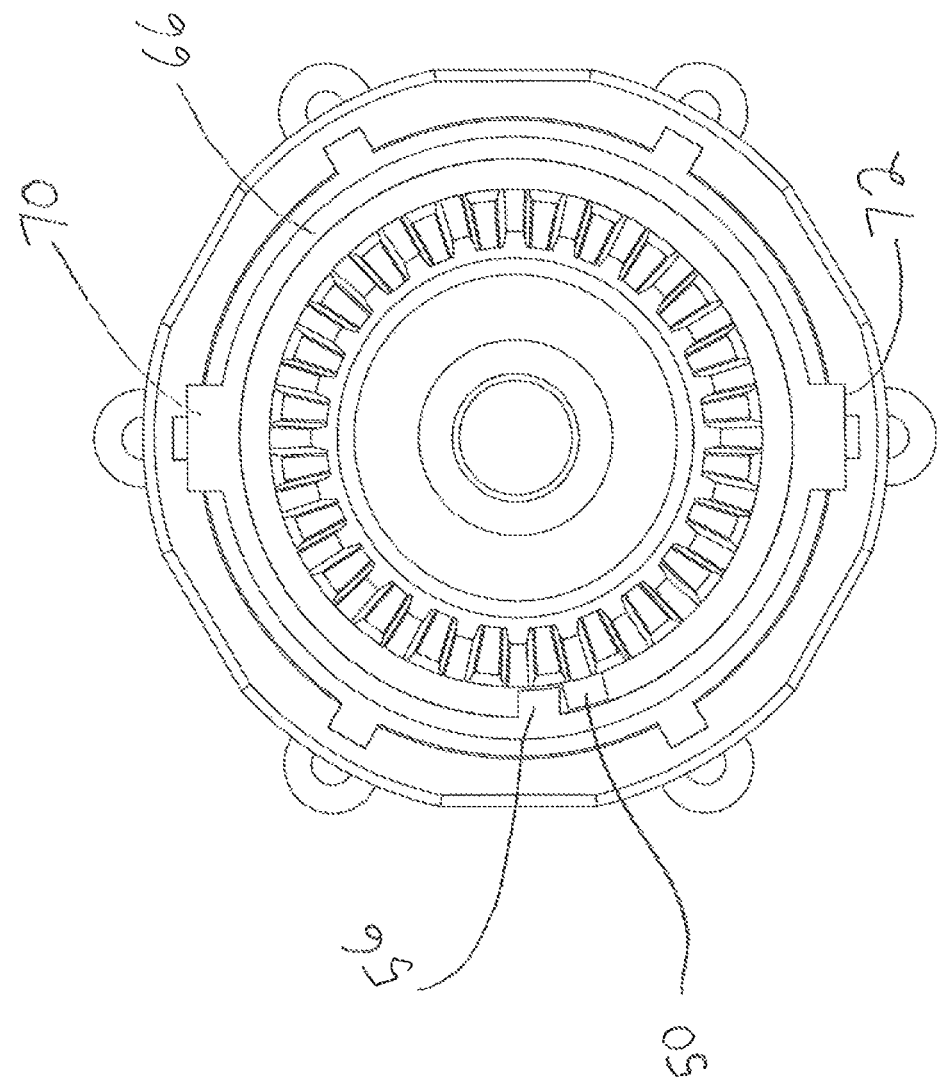

Referring now to FIGS. 9-11 the knob interference tab and handle stop will be now be discussed. In FIG. 9 the knob interference tab 50 is in the neutral or starting position. The handle stop interference tab is in a location 90 degrees counterclockwise or 270 degrees clockwise from the knob interference tab starting position. In this view, the knob 14 can be rotated clockwise or counterclockwise. As seen in FIG. 10, the knob has been rotated 90 degrees from the starting position in the counterclockwide direction and the knob interference tab 50 has engaged with the handle stop interference tab 56. The knob 14 can not be further rotated in the counterclockwise direction because the handle stop interference tab 56 interferes with the knob interference tab 50 and the knob 14 rotation is constrained in the counterclockwise. As seen in FIG. 11 the knob 14 has been rotated 270 degrees from the starting position in the clockwise direction and the knob interference tab 50 has engaged with the handle stop interference tab 56. The knob 14 cannot be further rotated in the clockwise direction because the handle stop interference tab 56 interferes with the knob interference tab 50 and the knob rotation is constrained in the clockwise direction.

The advantage of making the handle stop a separate component is that it adds more flexibility to the handle assembly design. If one wants to make a sheath with more or less deflection, instead of changing the entire handle design, one just drops in a different handle stop component. This is especially advantageous when the handle design is used with shafts of different sizes because the amount of pull wire travel to deflection angle is different for different sizes of shafts. Those of skill in the art will appreciate that with just the knob and handle stop configuration, the knob cannot be full rotated 360 degrees in either the clockwise or counterclockwise direction from the neutral starting position. This limitation is acceptable for uni-directional sheaths or bi-directional sheaths in which less deflection isn't necessary in both directions. For example, a sheath that deflects 90 degrees to the left and 180 degrees to the right.

Figure 12:
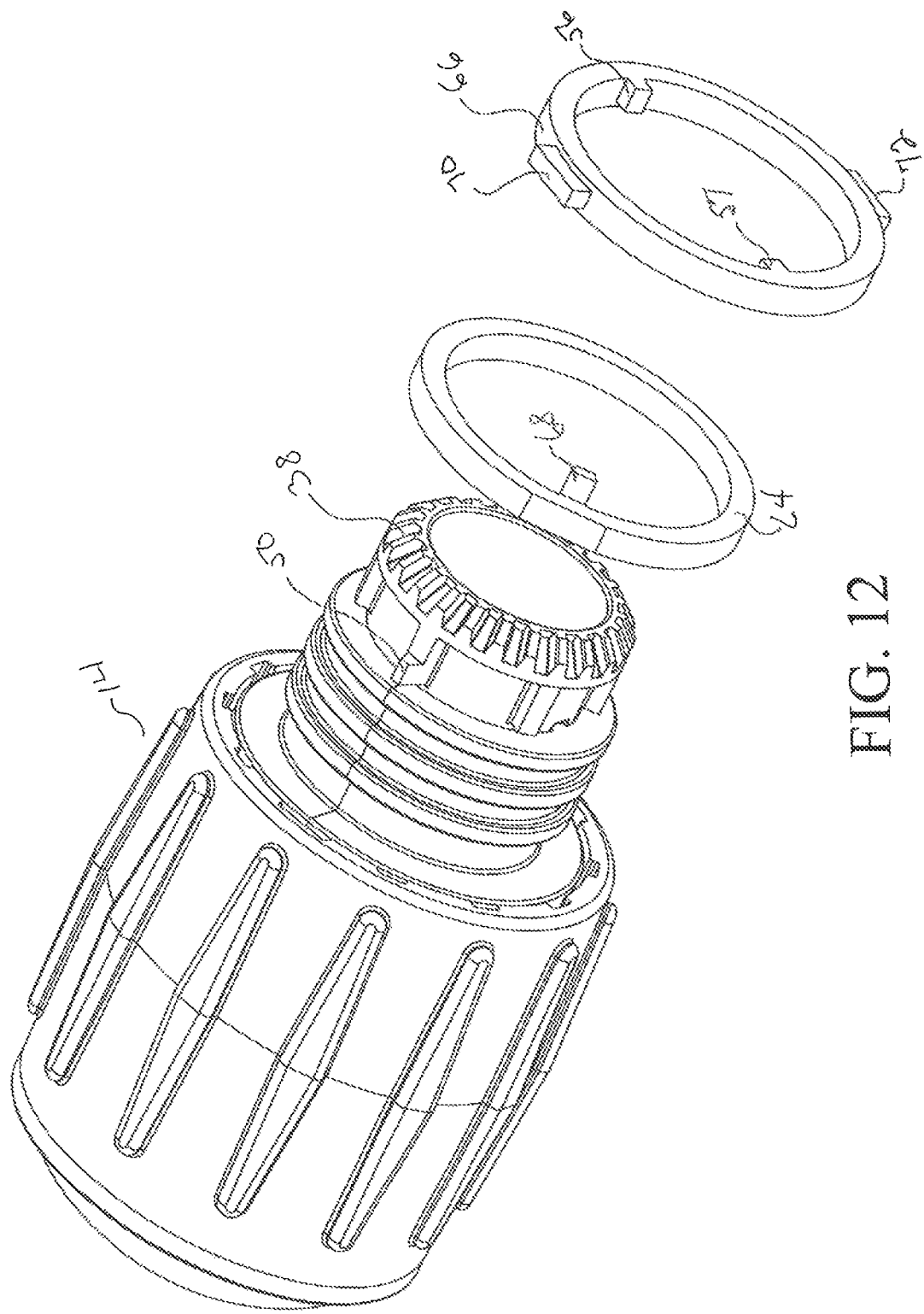
FIG. 12 is a partially exploded view of the knob showing the knob interference tab, floating stop and handle stop.

To address the rotational limitation of the knob and handle stop configuration, a floating stop 64 may be positioned between the knob 14 and handle stop 66 as best n in FIG. 12. The floating stop 64 includes interference tab 68 that interferes with both the knob interference tab 50 and the handle stop tabs 56, 57. The floating stop 64 also puts space between the knob interference tab 50 and the handle stop 66, such that the knob interference tab 50 does not engage with the interference tabs 56, 57 on the handle stop 66. In the starting or neutral position, the floating stop tab 68 is positioned between the knob interference tab 50 and one of the right or left handle stop interference tabs 56, 57. When the knob 14 is rotated in a direction away from the floating stop tab 68, it can be rotated a complete rotation because the knob interference tab does not engage with the interference tabs 56, 57 the handle stop 66. After one rotation, the knob interference tab 50 approaches the floating stop tab 68 from the other side. As knob rotation continues, the knob interference tab 50 interferes with and starts to push the floating stop tab 68. The knob interference tab 50 and floating stop tab 68 then rotate until the floating stop tab 68 engages the opposite interference tab 56, 57 on the handle stop 66. At this point, the knob 14 can no longer be rotated in this direction, but with the integration of the floating stop 64, the knob has been allowed to rotate an additional half turn. If the knob 14 is rotated in the opposite direction, it can be rotated 1.5 turns in that direction. Those of skill in the arts will appreciate that if the handle stop 66 included only one interference tab 56 or 57, the knob 14 would be able to rotate two complete rotations in either direction. Additionally, those of skill in the art will understand that by including additional floating stops 64, additional knob 14 rotations can be achieved. By way of example, by adding two floating stops, three knob rotations can be achieved. The advantage of this design is that the floating stops are a simple, small piece that add a minimal amount of length to the overall length of the handle. To allow more travel in the typical rotation translating mechanism, the handle overall length has to be increased or a more complex mechanism has to be integrated into the design.

Figure 13:
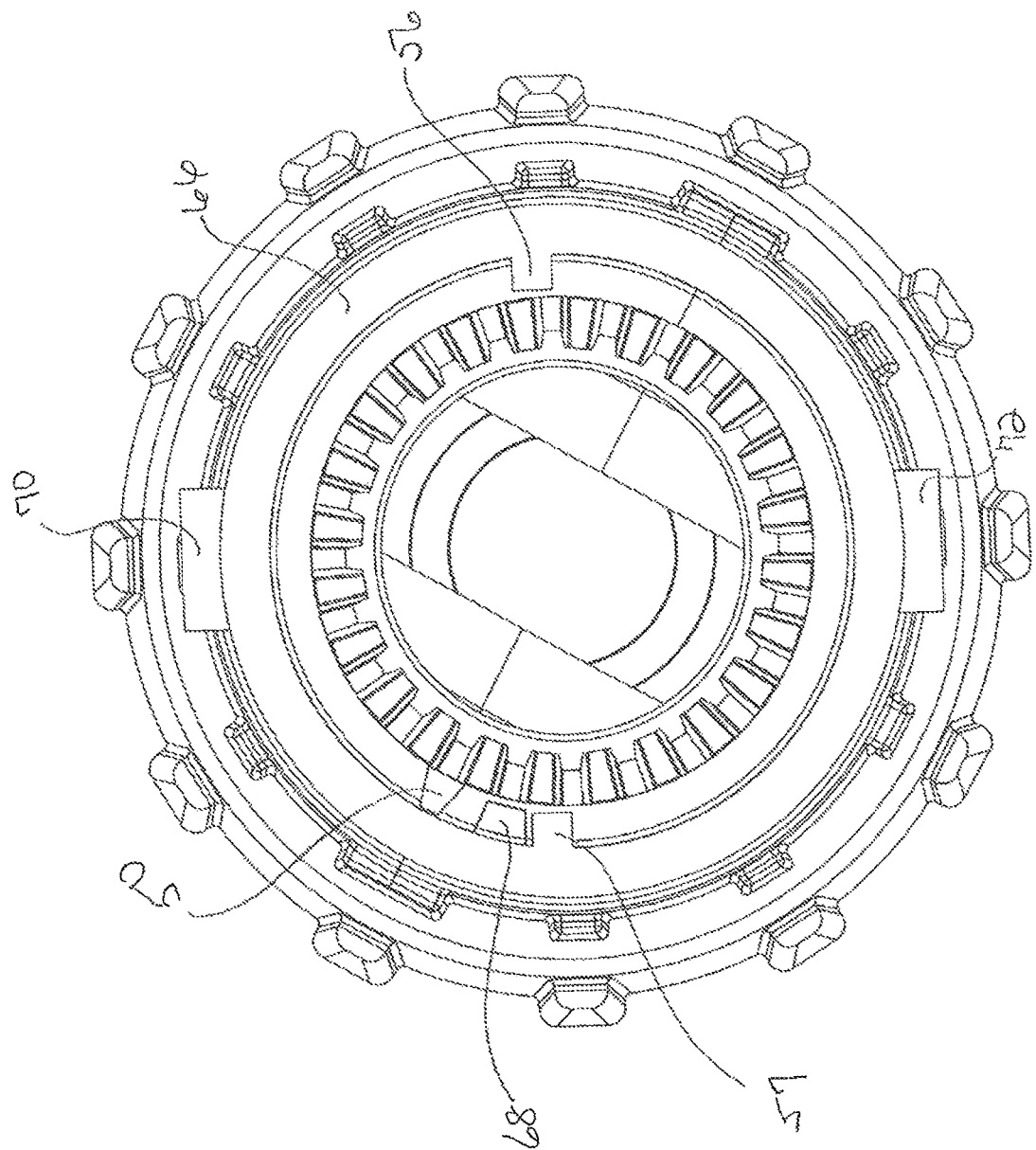
FIGS. 13-16 are front views of the knob showing the knob interference tab, floating stop and handle stop in the starting position, rotated a half-turn clockwise, full-turn clockwise and one and on-half turn clockwise positions, respectively.

Referring now to FIGS. 13-16 the floating stop 64 and interference tab 68 design will now be discussed. In FIG. 13 the floating stop interference tab 68 is shown the starting position between the left handle stop interference tab 57 and the knob interference tab 50. In this view, the knob 14 can only be rotated clockwise because the floating stop tab 68 engages with both the knob interference tab 50 and the handle stop interference tab 57 and prevents counter clockwise rotation of the knob 14.

Figure 14:
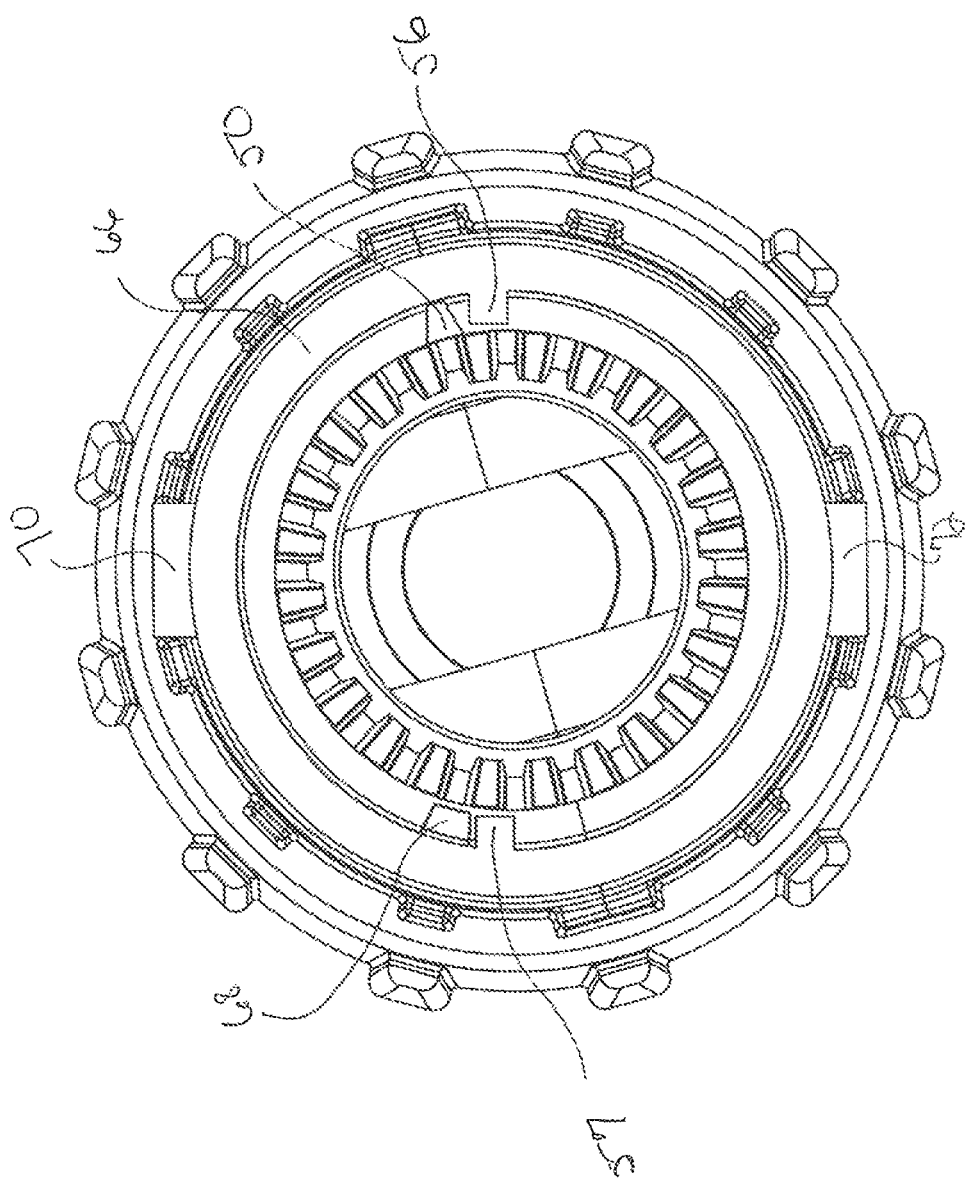
Figure 15:
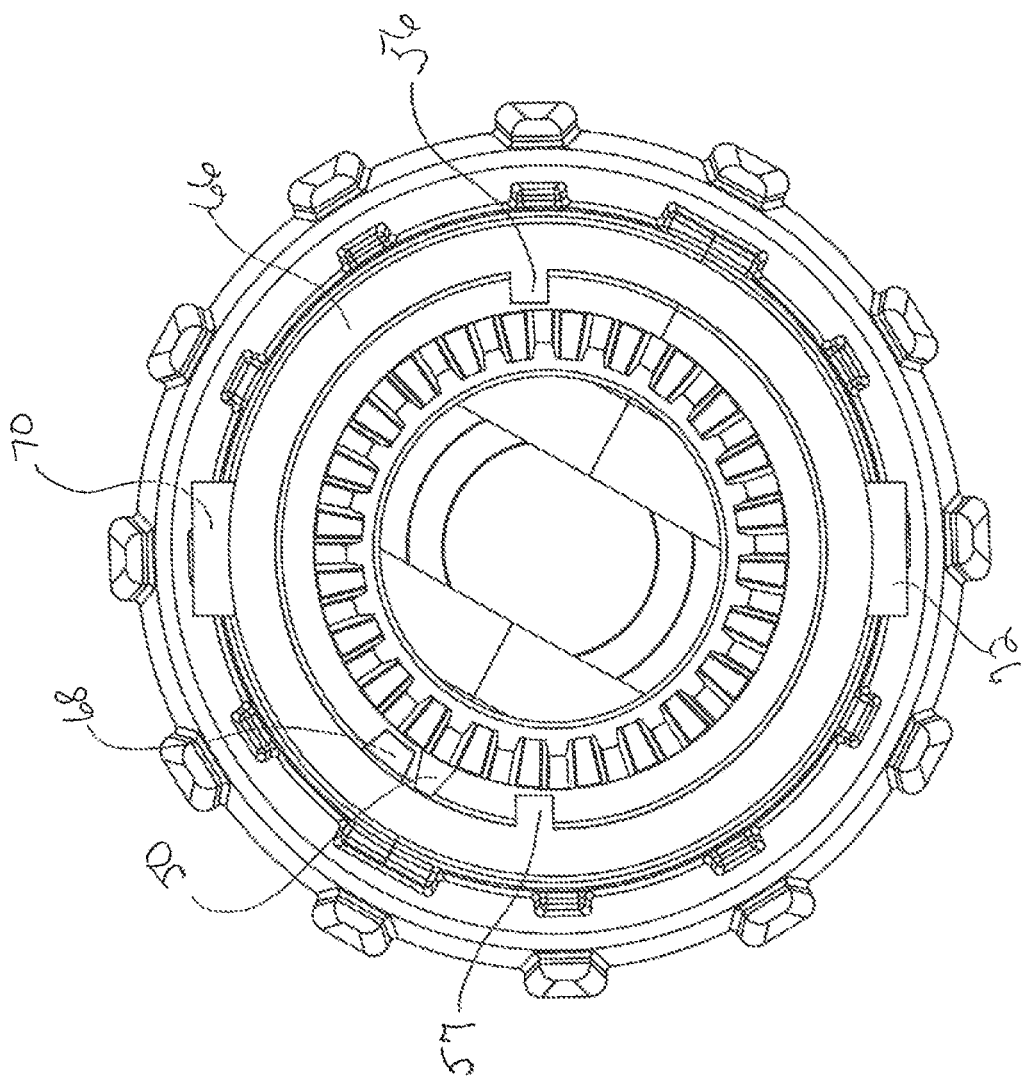
Figure 16:
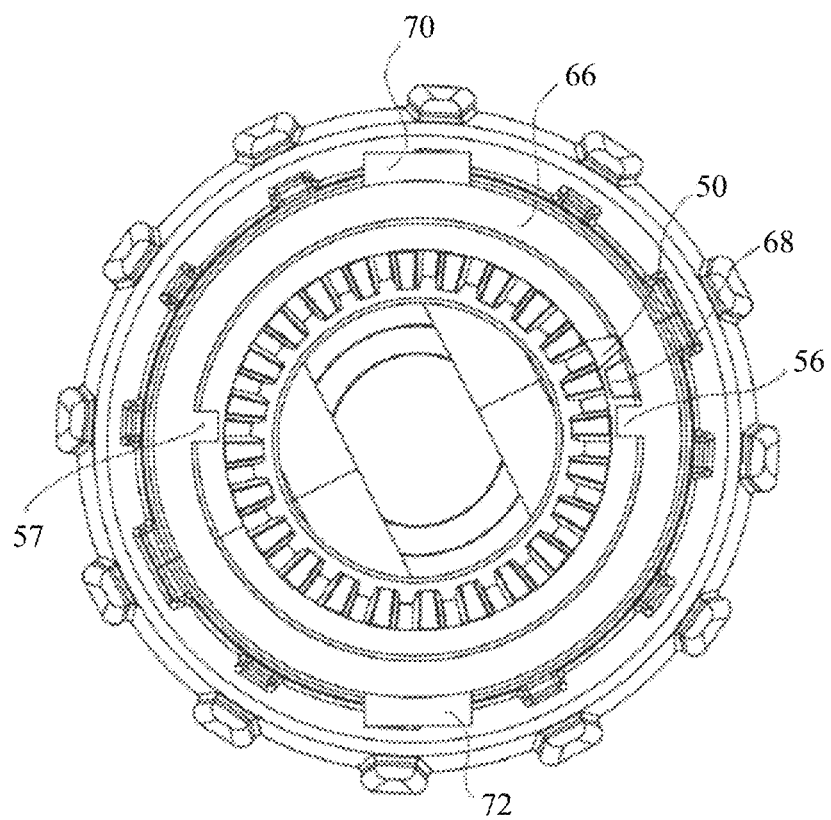

In FIG. 14 the knob 14 has been rotated a half turn clockwise but it can further rotate clockwise because the floating stop tab 68 is not between or engaging both the knob interference tab 50 and the right handle stop interference tab 56 on the handle stop 66. Thus, the knob interference tab 50 will not engage the right handle stop interference tab 56 on the handle stop 66. As see in FIG. 15 knob 14 leas been rotated more than a full turn clockwise. Knob 14 did not stop at the left handle stop interference tab 57 on handle stop 66 because the floating stop tab 68 was not between and therefore engaging both the knob interference tab 50 and the left handle stop interference tab 57 on handle stop 66. Thus, knob 14 can be further rotated clockwise. As seen in FIG. 16 knob 14 has been rotated 1.5 turns in the clockwise direction and will now stop because the floating stop tab 68 is between and engaging both the knob interference 50 and right handle stop interference tab 56 on handle stop 66. The knob 14 cannot be further rotated in the clockwise direction because the floating stop tab 68 interferes with or engages both the knob interference tab 50 and the right handle stop interference tab 56 on handle stop 66. The knob 14 can now be rotated in the counter clockwise direction 1.5 turns until it ends up in the starting position in which the floating stop tab 68 is between and engaging both the knob interference tab 50 and left handle stop interference tab 56 on handle stop 66.

Those of skill in the arts will appreciate that many modification should be made to the rotation knob bevel gear mechanism to achieve different outcomes. First, for example, only one bevel gear could be used which would create a uni-directional deflectable sheath.

Second, a second set of bevel gears and a second knob could be added to a control handle so that a shaft could be made quad-directional. In this case, the second set of gears would be offset 90 degrees from the first set of gears.

Third, the gear ratio between the rotation knob and bevel gear could be altered so that it is no longer 1 to 1. In one case, there could be more gear teeth on the knob to generate more deflection per rotation of the knob. In this situation, the knob would to be rotated less times to create full deflection. In the other case, the knob could have less teeth than the bevel gear, and this would give the user finer control over the sheath deflection.

Fourth, one bevel gear could have a different gear ratio to the knob that the other bevel gear to give the user the to ability to deflect to left or right with different attributes (i.e. fine control to the right, but quick, gross control to the left).

Figure 17:
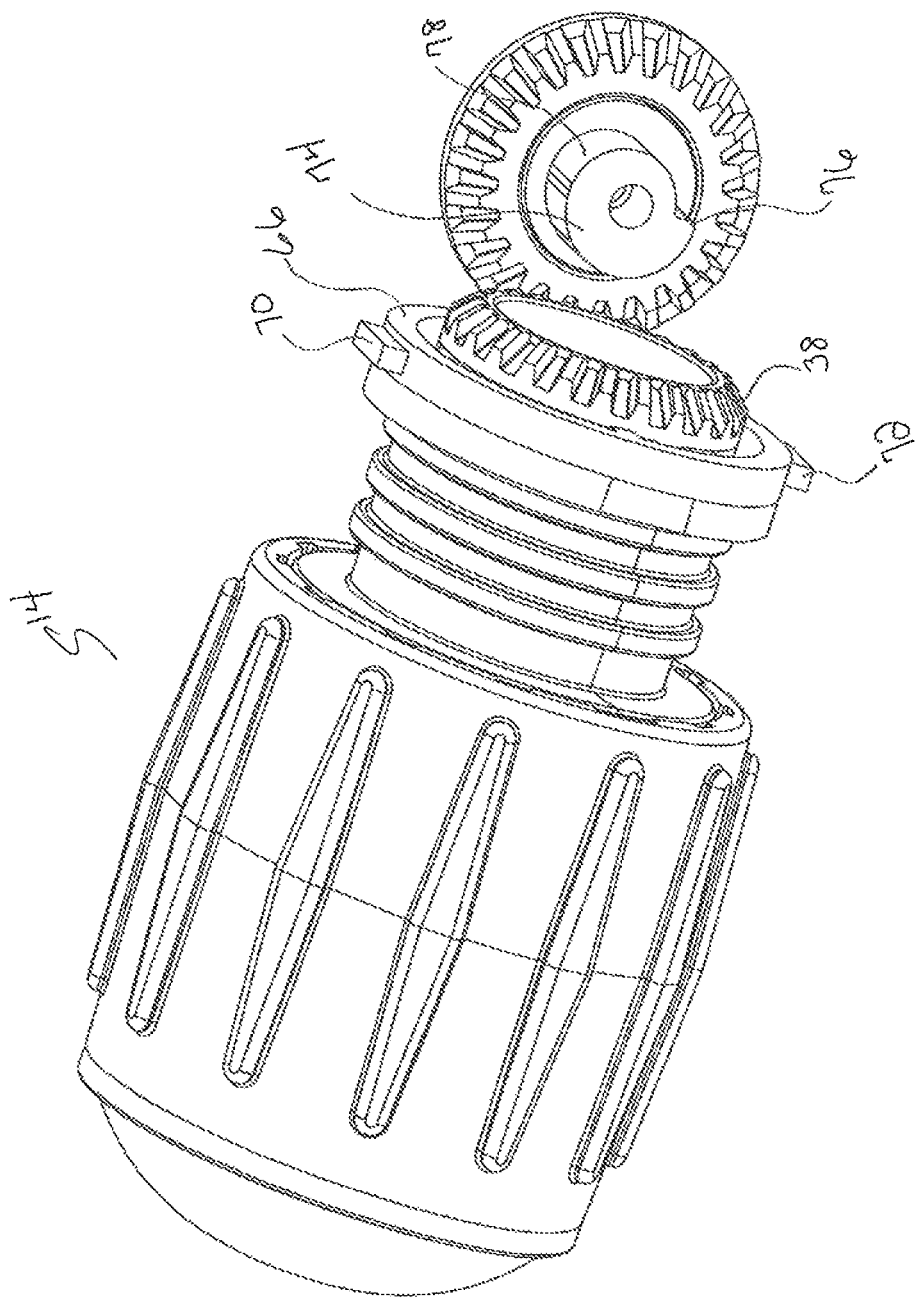
FIGS. 17-19 are perspective views of the control knob showing the rotation of the cam wrapping bevel gear as it rotates through three positions.
Figure 18:
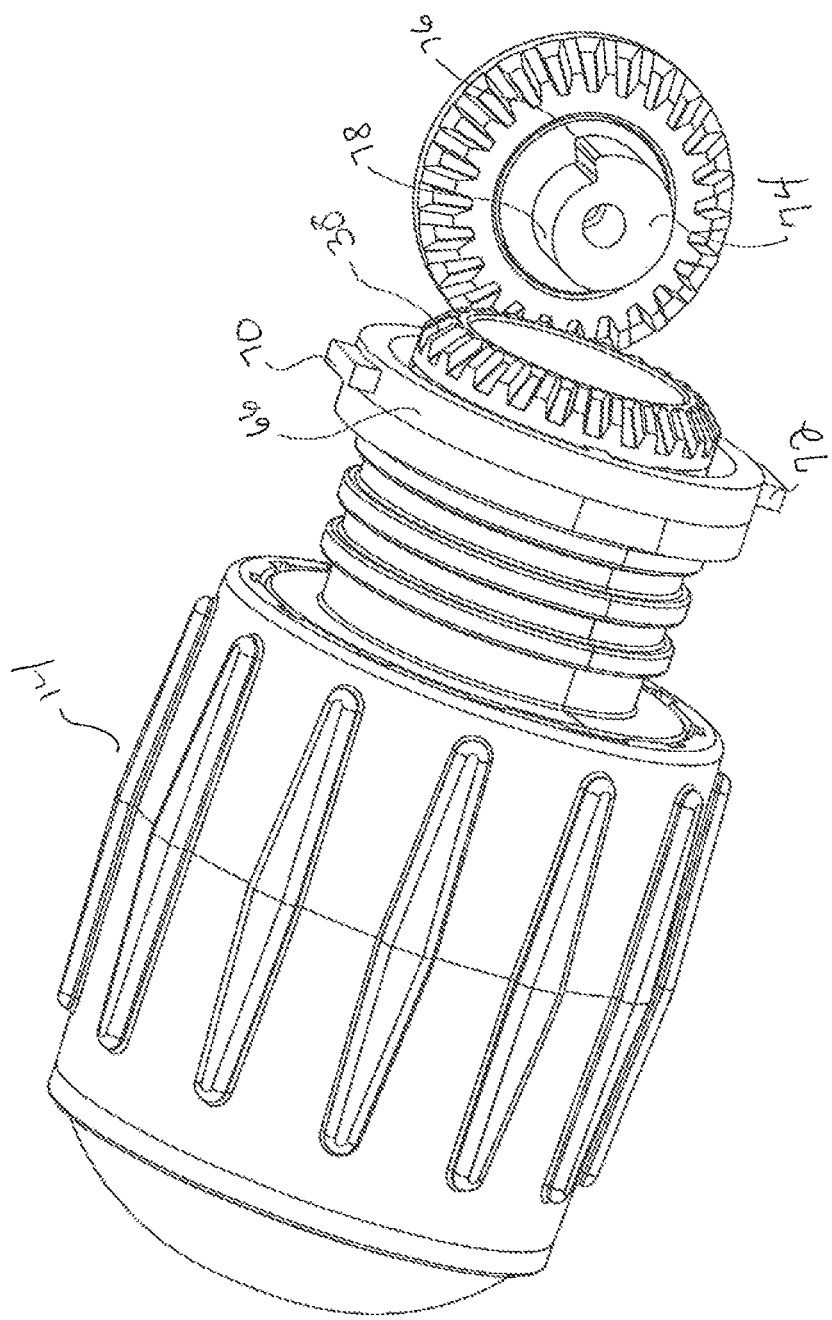
Figure 19:
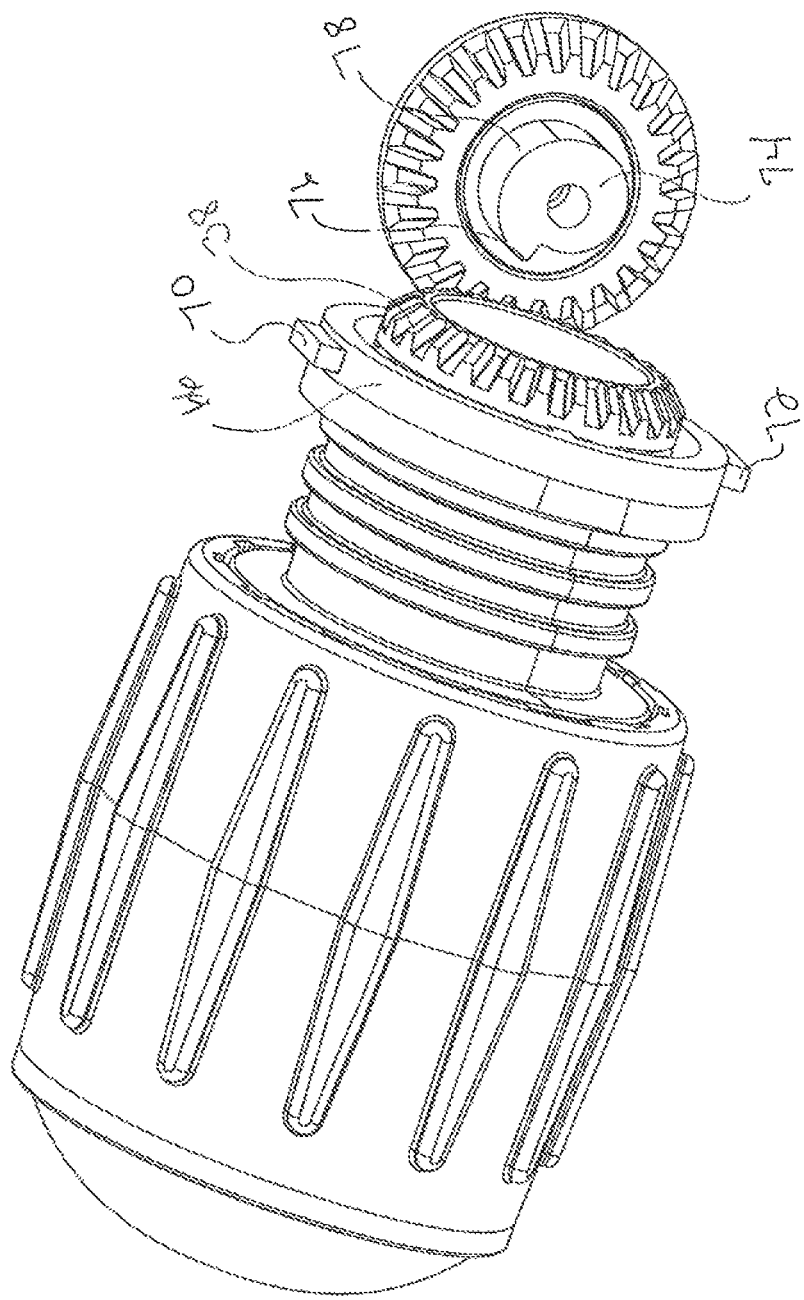

Fifth, the bevel gear surface could have a cam shape rather than a circular shape as seen in FIGS. 17-19 showing the rotation of an alternative cam wrapping bevel gear 74 as it rotates through three positions is shown. The pull wire wrapping point 76 includes a first part of the wrapping surface that has a diameter greater than the diameter of the remainder of the wrapping surface 78. Thus as the adjustment knob 14 rotates and the bevel gear rotates, the diameter of the wrapping surface 78 decreases. After almost a full rotation, as best seen in FIG. 19, the bevel gear wrapping surface 78 is at its smallest diameter.

The cam shape could be designed to increase or decrease the rate of deflection depending on the point in the knob rotation. For example, it is known to those of skill in the arts that there is not a linear relationship between the amount of pull wire translation and distal sheath deflection. This means there is not a linear relationship between the amount of knob rotation and distal sheath deflection. It takes more pull wire translation to accomplish the deflection of the sheath from 0-90 degrees than it does for sheath deflection angles greater than 90 degrees. Thus, the first half turn or so of the knob will cause the heat deflect 90 degrees, but it will only take another quarter turn of the knob to deflect the sheath to 180 degrees. This means that the user of the sheath needs to understand that depending on how far the sheath has been deflected, subsequent rotating of the knob will not translate to the same amount of sheath deflection as the previous amount of deflection. It can be difficult for the sheath user to keep track of this relationship and every sheath on the market has a slightly different knob rotation to sheath deflections relationship. With a cam shaped wrapping surface, the diameter of the cam could be varied so that depending on how much the knob has been rotated, the pull wire is translated at a rate that maintains a linear relationship between knob rotation and sheath deflection. One design for such a CAM would have a larger wrapping diameter to correspond to the initial rotation of the knob to the point where the distal shaft has deflected about or to 90 degrees. After 90 degree deflection point, the can wrapping diameter would start to decrease so that further rotation of the knob accomplished a more gradual deflection of the sheath from 90 to 180 degrees and thereby giving the user a more consistent and linear relationship between knob rotation and distal sheath deflection.

A main advantage of the rotation knob to bevel gear mechanism in accordance with the invention is that it is very compact and thus allows the steerable sheath to have a shorter, smaller handle without sacrificing the ability to d fleet the sheath to a high degree. It is also a simpler design with less components than the typical knob-lead screw mechanism, and it is easier to put together than the typical knob-lead screw mechanism. Also, the knob in this mechanism requires no internal thread, which makes it much easier to produce with injection molding, the standard process for producing sheath handle components. The simple design ease of assembly, and knob with no internal thread add up to a control handle design that has a lower cost and a more consistent assembly process (less scrap).

Finally, in the cam embodiment the bevel gear wrapping surface has a cam shape, and the knob to bevel mechanism allows for a 1 to 1 ratio of knob rotation to pull wire movement. This creates a more intuitive understanding of the amount of sheath handle deflection based on knob rotation, therefore imparting more control to the clinician. Furthermore, the 1 to 1 ratio of knob rotation to pull wire movement requires the user to rotate the knob less during a longer procedure, which in turn helps prevent hand fatigue and repetitive stress injuries.

In one aspect of the transfer assembly, the pull ring is eliminated. Each pull wire is run up the wall of the sheath shaft, wrapped in a loop around the shaft, and then ran back down the wall of the shaft. Thus, each pull wire is doubled as it travels down the wall of the sheath shaft. At the beginning of the transfer assembly manufacturing process, each pull wire loop is located on the outside of the sheath shaft. The pull wires are looped so that they are disposed 180 degrees. A section of higher durometer PEBAX or similar thermoplastic is located just behind the pull wire loops.

After the loops have been formed and both sections of each pull wire exit the sheath shaft, the tip of the shaft is subjected to heat and the pull wires are pulled proximally. During this process, the higher durometer thermoplastic melts and the pull wire loops become encased. When the thermoplastic cools down, a robust pull wire shaft connection has been formed.

Another advantage of the deflection mechanism in accordance with the invention is that it is MR compatible. Second, it eliminates a component, the pull ring, so it simplifies manufacturing and lowers the overall cost. Finally, preliminary benchmark testing has shown that this design has a higher tensile strength than the traditional metallic designs and the polymeric pull wire to polymeric pull ring designs.

Although the invention has been described with reference to certain aspects and embodiments, those of skill in the art will appreciate that changes may be made in form and detail without departing from the spirit and scope of the invention.

What is claimed:

1. A deflectable sheath assembly, comprising:
    a tubular shaft receiving first and second longitudinal movement wires operably coupled to a distal end thereof;
    a control handle having a main body configured to receive first and second bevel gears having teeth on a surface thereof, the first longitudinal movement wire operably coupled to the first bevel gear and the second longitudinal movement wire operably coupled to the second bevel gear;
    a rotatable adjustment knob operably engageable with the control handle, the rotatable adjustment knob having an external geared portion matingly engageable with the first and second bevel gears, the rotatable adjustment knob moveable at least between a first and a second position,
    wherein in rotation to the first position the rotatable adjustment knob engages the teeth of the first bevel gear and causes the first bevel gear to rotate in a direction that causes the first longitudinal pull wire to wrap around a surface of the first bevel gear to cause proximal longitudinal movement of the first longitudinal movement wire,
    and further wherein in the rotation to the first position the rotatable adjustment knob engages the teeth of the second bevel gear and causes the second bevel gear to rotate in a direction that causes the second longitudinal pull wire to unwrap around a surface of the second bevel gear and cause tension to be released on the second longitudinal movement wire,
    and further wherein in the rotation to the second position the rotatable adjustment knob engages the teeth of the second bevel gear and causes the second bevel gear to rotate in a direction that causes the second longitudinal pull wire to wrap around a surface of the second bevel gear and cause proximal longitudinal movement of the second longitudinal movement wire,
    and further wherein in the rotation to the second position the rotatable adjustment knob causes engagement of the teeth on the first bevel gear and cause the first bevel gear to rotate in a direction that causes the first longitudinal pull wire to unwrap around a surface of the first bevel gear and cause tension to be released on the first longitudinal movement wire;
    and further wherein the deflectable sheath assembly further comprises a floating stop component disposed between the rotatable adjustment knob and a separate handle stop component, and an interference tab on the floating stop that is configured to interfere with both a knob interference tab on an outer surface of the rotatable adjustment knob and an interference tab on the separate handle stop component and allows for the rotatable adjustment knob to rotate one or more revolutions before being stopped.

2. The deflectable sheath assembly of claim 1, wherein proximal longitudinal movement of the first longitudinal movement wire causes the distal end of the steerable sheath to deflect from a longitudinal axis of the tubular shaft in a first direction.

3. The deflectable sheath assembly of claim 1, wherein the proximal longitudinal movement of the second longitudinal movement wires causes the distal end of the steerable sheath to deflect from a longitudinal axis of the tubular shaft in a second direction.

4. The deflectable sheath assembly of claim 1, wherein the first longitudinal movement wire is positioned within a wall of a distal section of the tubular shaft.

5. The deflectable sheath assembly of claim 1, wherein the second longitudinal movement wire is positioned within the wall of a distal section of the tubular shaft.

6. The deflectable sheath assembly of claim 1, wherein the control handle includes first and second handle halves.

7. The deflectable sheath assembly of claim 1, further including a pull wire housing component for preventing slack in the first and second longitudinal movement wires from getting tangled in other handle components.

8. The deflectable sheath assembly of claim 1, wherein a proximal portion of the first and second longitudinal movement wires comprise a flexible polymer.

9. The deflectable sheath assembly of claim 1, wherein a distal portion of the first and second longitudinal movement wires comprises stainless steel.

10. The deflectable sheath assembly of claim 1, wherein the knob interference tab does not engage with the interference tab on the separate handle stop component.

11. The deflectable sheath assembly of claim 1, further comprising a second set of a knob, bevel gears, and longitudinal pull wires to create a sheath that has quad-directional deflection.

12. The deflectable sheath assembly of claim 1, in which the gear ratio between the rotation knob and each of the bevel gears is different than 1:1.

13. The deflectable sheath assembly of claim 1, in which the wrapping surface of the bevel gear has a non-circular shape selected from a tear-drop or other cam shape.

14. The deflectable sheath assembly of claim 6, wherein the first and second handle halves are positioned within a lumen of a keystone component.

15. The deflectable sheath assembly of claim 8, wherein the proximal portion of the first and second longitudinal movement wires wraps around the surface of the first and second bevel gears.

16. The deflectable sheath assembly of claim 9, further comprising a wire-bridge component that operably couples the distal portions of the first and second longitudinal movement wires with a proximal portion of the first and second longitudinal movement wires.

17. The deflectable sheath assembly of claim 15 wherein a surface of the first and second bevel gears has a circumference.

18. The deflectable sheath assembly of claim 12, in which the gear ratio between the rotation knob and the first bevel gear is different than the gear ratio between the rotation knob and the second bevel gear.

19. A deflectable sheath assembly, comprising:
- a tubular shaft receiving first and second longitudinal movement wires operably coupled to a distal end thereof;
- a control handle having a main body configured to receive first and second bevel gears having teeth on a surface thereof, the first longitudinal movement wire operably coupled to the first bevel gear and the second longitudinal movement wire operably coupled to the second bevel gear;
- a rotatable adjustment knob operably engageable with the control handle, the rotatable adjustment knob having an external geared portion matingly engageable with the first and second bevel gears, the rotatable adjustment knob moveable at least between a first and a second position, wherein in rotation to the first position the rotatable adjustment knob engages the teeth of the first bevel gear and causes the first bevel gear to rotate in a direction that causes the first longitudinal pull wire to wrap around a surface of the first bevel gear to cause proximal longitudinal movement of the first longitudinal movement wire, and further wherein in the rotation to the first position the rotatable adjustment knob engages the teeth of the second bevel gear and causes the second bevel gear to rotate in a direction that causes the second longitudinal pull wire to unwrap around a surface of the second bevel gear and cause tension to be released on the second longitudinal movement wire, and further wherein in the rotation to the second position the rotatable adjustment knob engages the teeth of the second bevel gear and causes the second bevel gear to rotate in a direction that causes the second longitudinal pull wire to wrap around a surface of the second bevel gear and cause proximal longitudinal movement of the second longitudinal movement wire, and further wherein in the rotation to the second position the rotatable adjustment knob causes engagement of the teeth on the first bevel gear and cause the first bevel gear to rotate in a direction that causes the first longitudinal pull wire to unwrap around a surface of the first bevel gear and cause tension to be released on the first longitudinal movement wire;

wherein the deflectable sheath assembly further comprises a floating stop component disposed between the rotatable adjustment knob and a separate handle stop component; and wherein two or more floating stop components are disposed between the rotatable adjustment knob and the control handle that are configured to allow the rotatable adjustment knob to rotate two or more revolutions before being stopped.

\* \* \* \* \*